United States Patent
He et al.

(10) Patent No.: US 12,364,646 B1
(45) Date of Patent: Jul. 22, 2025

(54) METHOD AND APPARATUS FOR LOCATING HEAD SIDE ACUPUNCTURE POINTS, MOXIBUSTION ROBOT, AND STORAGE MEDIUM

(71) Applicant: Jianghan University, Wuhan (CN)

(72) Inventors: Qiang He, Wuhan (CN); Yifan Deng, Wuhan (CN); Lixin Yu, Wuhan (CN); Hongxing Zhang, Wuhan (CN); Qian Tu, Wuhan (CN)

(73) Assignee: Jianghan University, Wuhan (CN)

( * ) Notice: Subject to any disclaimer, the term of this patent is extended or adjusted under 35 U.S.C. 154(b) by 0 days.

(21) Appl. No.: 18/939,139

(22) Filed: Nov. 6, 2024

(30) Foreign Application Priority Data

Jun. 17, 2024 (CN) .......................... 202410776344.5

(51) Int. Cl.
*A61H 39/02* (2006.01)
*A61B 34/30* (2016.01)

(52) U.S. Cl.
CPC ............ *A61H 39/02* (2013.01); *A61B 34/30* (2016.02)

(58) Field of Classification Search
CPC ................................ A61H 39/02; A61B 34/30
See application file for complete search history.

(56) References Cited

FOREIGN PATENT DOCUMENTS

| CN | 113807414 A | 12/2021 |
|---|---|---|
| CN | 118340664 A | 7/2024 |

OTHER PUBLICATIONS

Zhang, Menghe ("FaceAtlasAR: Atlas of Facial Acupuncture Points in Augmented Reality") Computer Science & Information Technology (Year: 2021).*

First Office Action, issued by National Intellectual Property Administration fo the People's Republic of China, CN App. 202410776344. 5, issued Jul. 23, 2024.

* cited by examiner

*Primary Examiner* — Molly Wilburn
(74) *Attorney, Agent, or Firm* — Thomas | Horstemeyer, LLP

(57) ABSTRACT

A method and apparatus for locating head side acupuncture points, a moxibustion robot, and a storage medium are provided. The method includes: training an acupuncture point identification model based on a head side acupuncture point sample set to obtain a target acupuncture point identification model, where the head side acupuncture point sample set includes a plurality of acupuncture point sample points and a plurality of support sample points in a curve of gallbladder meridian of foot-shaoyang; inputting a head side image to be identified to the target acupuncture point identification model to obtain a plurality of acupuncture points and a plurality of support points; fitting the plurality of acupuncture points and the plurality of support points to obtain a fitted curve; and determining whether the acupuncture points require correction based on the fitted curve, if yes, correcting the acupuncture points based on the fitted curve to obtain target acupuncture points.

16 Claims, 7 Drawing Sheets

S401 — When the curvature variation rate of the sub-curve of gallbladder meridian of foot-shaoyang is less than or equal to a first threshold, a total number of support sample points and acupuncture point sample points in the sub-curve of gallbladder meridian of foot-shaoyang be a first threshold number, and determine a target number of support sample points inserted to the sub-curve of gallbladder meridian of foot-shaoyang based on the first threshold number and the number of the acupuncture point sample points S402 — When the curvature variation rate of the sub-curve of gallbladder meridian of foot-shaoyang is greater than the first threshold and the curve length of the sub-curve of gallbladder meridian of foot-shaoyang is less than or equal to a length threshold, the total number of support sample points and acupuncture point sample points in the sub-curve of gallbladder meridian of foot-shaoyang be a second threshold number, and determine a target number of support sample points inserted to the sub-curve of gallbladder meridian of foot-shaoyang based on the second threshold number and the number of the acupuncture point sample points S403 — When the curvature variation rate of the sub-curve of gallbladder meridian of foot-shaoyang is greater than the first threshold and the curve length of the sub-curve of gallbladder meridian of foot-shaoyang is greater than the length threshold, the total number of support sample points and acupuncture point sample points in the sub-curve of gallbladder meridian of foot-shaoyang be a third threshold number, and determine a target number of support sample points inserted to the sub-curve of gallbladder meridian of foot-shaoyang based on the third threshold number and the number of the acupuncture point sample points S404 — Insert the target number of support sample points to the sub-curve of gallbladder meridian of foot-shaoyang

FIG. 4

METHOD AND APPARATUS FOR LOCATING HEAD SIDE ACUPUNCTURE POINTS, MOXIBUSTION ROBOT, AND STORAGE MEDIUM

CROSS REFERENCE TO RELATED APPLICATION

This patent application claims the benefit and priority of Chinese Patent Application No. 202410776344.5, filed with the China National Intellectual Property Administration on Jun. 17, 2024, the disclosure of which is incorporated by reference herein in its entirety as part of the present application.

TECHNICAL FIELD

The present disclosure relates to the technical field of identification of acupuncture points, and in particular, to a method and apparatus for locating head side acupuncture points, a moxibustion robot, and a storage medium.

BACKGROUND

The head of a human body has 9 meridians: stomach meridian of foot-yangming, gallbladder meridian of foot-shaoyang, bladder meridian of foot-taiyang, large intestine meridian of hand-yangming, sanjiao meridian of hand-shaoyang, small intestine meridian of hand-taiyang, conception meridian, governor meridian, and liver meridian of foot-jucyin. The head also has many acupuncture points, including Yangbai, Xuanlu, Qubin, Jiaosun, Luxi, Benshen, Toulinqi, Chengling, Naokong, Hanyan, Shangguan, etc. Head side acupuncture points have been widely used in health care and medical applications. Different acupuncture points have different efficacies. The head side acupuncture points have important significance and efficacies in health care and medical applications.

At present, the identification and locating of the head side acupuncture points mainly rely on the experience and skills of doctors of traditional Chinese medicine accumulated for a long time. A doctor may manually analyze the head features of a patient and then approximately determine the positions of the acupuncture points on the head in combination with the theoretical knowledge of directions and distribution of meridians and collaterals on the head. However, this traditional method has the problems of strong individual subjectivity, different judgments of different doctors on the same patient, inconsistent acupuncture point locating results, etc. In addition, the determination of acupuncture points may take a lot of time and energy, which has low efficiency and high requirements on the experience of the doctors of traditional Chinese medicine.

There is an urgent need to provide a method and apparatus for locating head side acupuncture points, a moxibustion robot, and a storage medium so as to improve the accuracy and efficiency of locating the head side acupuncture points, assist doctors with diagnosing a patient's condition, and ease a doctor's burden.

SUMMARY

In view of the above, it is necessary to provide a method and apparatus for locating head side acupuncture points, a moxibustion robot, and a storage medium to solve the technical problem of low accuracy of locating head side acupuncture points in the prior art.

In an aspect, in order to solve the above technical problem, the present disclosure provides a method for locating head side acupuncture points, including:
training an acupuncture point identification model based on a head side acupuncture point sample set to obtain a target acupuncture point identification model, where the head side acupuncture point sample set includes a plurality of acupuncture point sample points and a plurality of support sample points in a curve of gallbladder meridian of foot-shaoyang;
inputting a head side image to be identified to the target acupuncture point identification model to obtain a plurality of acupuncture points and a plurality of support points;
fitting the plurality of acupuncture points and the plurality of support points to obtain a fitted curve; and
determining whether the acupuncture points require correction based on the fitted curve, and if yes, correcting the acupuncture points based on the fitted curve to obtain target acupuncture points.

In a possible implementation, before the training an acupuncture point identification model based on a head side acupuncture point sample set, the method further includes:
acquiring a plurality of head side sample images, and determining the curve of gallbladder meridian of foot-shaoyang in each of the head side sample images;
marking acupuncture points based on the curve of gallbladder meridian of foot-shaoyang to obtain the plurality of acupuncture point sample points;
segmenting the curve of gallbladder meridian of foot-shaoyang based on inflection points of the curve of gallbladder meridian of foot-shaoyang to obtain a plurality of sub-curves of gallbladder meridian of foot-shaoyang; and
determining, based on a number of the acupuncture point sample points in each of the sub-curves of gallbladder meridian of foot-shaoyang and a curve feature, at least one support sample point inserted to the sub-curve of gallbladder meridian of foot-shaoyang.

In a possible implementation, the curve feature includes a curvature variation rate and a curve length; and the determining, based on a number of the acupuncture point sample points in each of the sub-curves of gallbladder meridian of foot-shaoyang and a curve feature, at least one support sample point inserted to the sub-curve of gallbladder meridian of foot-shaoyang includes:
when the curvature variation rate of the sub-curve of gallbladder meridian of foot-shaoyang is less than or equal to a first threshold, a total number of support sample points and acupuncture point sample points in the sub-curve of gallbladder meridian of foot-shaoyang being a first threshold number, and determining a target number of support sample points inserted to the sub-curve of gallbladder meridian of foot-shaoyang based on the first threshold number and the number of the acupuncture point sample points;
when the curvature variation rate of the sub-curve of gallbladder meridian of foot-shaoyang is greater than the first threshold and the curve length of the sub-curve of gallbladder meridian of foot-shaoyang is less than or equal to a length threshold, the total number of support sample points and acupuncture point sample points in the sub-curve of gallbladder meridian of foot-shaoyang being a second threshold number, and determining a target number of support sample points inserted to the sub-curve of gallbladder meridian of foot-shaoyang based on the second threshold number and the number of the acupuncture point sample points;

when the curvature variation rate of the sub-curve of gallbladder meridian of foot-shaoyang is greater than the first threshold and the curve length of the sub-curve of gallbladder meridian of foot-shaoyang is greater than the length threshold, the total number of support sample points and acupuncture point sample points in the sub-curve of gallbladder meridian of foot-shaoyang being a third threshold number, and determining a target number of support sample points inserted to the sub-curve of gallbladder meridian of foot-shaoyang based on the third threshold number and the number of the acupuncture point sample points; and inserting the target number of support sample points to the sub-curve of gallbladder meridian of foot-shaoyang;

where the first threshold number is less than the second threshold number, and the second threshold number is less than the third threshold number.

In a possible implementation, the fitting the plurality of acupuncture points and the plurality of support points to obtain a fitted curve includes:

determining a plurality of curve segments based on the plurality of acupuncture points and the plurality of support points, where the curve segments are gentle curve segments or circular curve segments; and each of the curve segments includes at least one of the acupuncture points and at least one of the support points.

In a possible implementation, the determining whether the acupuncture points require correction based on the fitted curve includes:

determining whether a distance between each of the acupuncture points and the fitted curve is greater than zero and less than a distance threshold;

when the distance between each of the acupuncture points and the fitted curve is equal to zero, the acupuncture point needing not to be corrected;

when the distance between each of the acupuncture points and the fitted curve is greater than or equal to the distance threshold, removing the acupuncture point; and when the distance between each of the acupuncture points and the fitted curve is greater than zero and less than the distance threshold, the acupuncture point needing to be corrected.

In a possible implementation, the correcting the acupuncture points based on the fitted curve to obtain target acupuncture points includes:

acquiring a tangent line of the fitted curve, and using a direction in which the tangent line is perpendicular to and points to the fitted curve as a moving direction of the acupuncture point; and using a distance between the acupuncture point and the fitted curve as a moving distance, and controlling the acupuncture point to move by the moving distance along the moving direction to obtain the target acupuncture point.

In a possible implementation, the head side acupuncture point sample set includes a plurality of head side sample images of different persons, a plurality of head side sample images of a same person by a same distance at different angles, and a plurality of head side sample images of a same person by different distances at a same angle.

In another aspect, the present disclosure further provides an apparatus for locating head side acupuncture points, including:

a model training unit configured to train an acupuncture point identification model based on a head side acupuncture point sample set to obtain a target acupuncture point identification model, where the head side acupuncture point sample set includes a plurality of acupuncture point sample points and at least one support sample point in a curve of gallbladder meridian of foot-shaoyang;

an image identification unit configured to input a head side image to be identified to the target acupuncture point identification model to obtain a plurality of acupuncture points and a plurality of support points;

a curve fitting unit configured to fit the plurality of acupuncture points and the plurality of support points to obtain a fitted curve; and an acupuncture point locating unit configured to determine whether the acupuncture points require correction based on the fitted curve, and if yes, correct the acupuncture points based on the fitted curve to obtain target acupuncture points.

In another aspect, the present disclosure further provides a moxibustion robot, including a memory and a processor, where:

the memory is configured to store a program; and the processor is coupled with the memory and configured to execute the program stored in the memory to implement the steps of the method for locating head side acupuncture points in any of the above possible implementations.

In another aspect, the present disclosure further provides a computer readable storage medium, storing a program or instructions which, when executed by a processor, cause(s) the steps of the method for locating head side acupuncture points in any of the above possible implementations to be implemented.

The present disclosure has the beneficial effects: the method for locating head side acupuncture points provided in the present disclosure uses the target acupuncture point identification model (i.e., a deep learning model) to identify acupuncture points, and can case a doctor's burden and improve the identification efficiency of head side acupuncture points. Moreover, the head side acupuncture point sample set in the present disclosure includes a plurality of acupuncture point sample points and a plurality of support sample points in the curve of gallbladder meridian of foot-shaoyang. That is, the acupuncture point sample points are restrained to be in the curve of gallbladder meridian of foot-shaoyang. The accuracy of the acupuncture points in the head side acupuncture point samples can be guaranteed, and then the accuracy of the acupuncture points identified based on the target acupuncture point identification model can be improved. That is, the locating accuracy of head side acupuncture points is improved.

Further, the present disclosure further involves fitting the identified plurality of acupuncture points and the identified plurality of support points to obtain the fitted curve. The acupuncture points needing to be corrected are corrected based on the fitted curve such that the accuracy of the determined target acupuncture points is further improved. That is, the locating accuracy of head acupuncture points is further improved.

BRIEF DESCRIPTION OF THE DRAWINGS

In order to describe the technical solutions in the embodiments of the present invention more clearly, the accompanying drawings required to describe the embodiments are briefly described below. Apparently, the accompanying drawings in the following description show merely some embodiments of the present disclosure, and those skilled in the art may still derive other accompanying drawings from these accompanying drawings without creative efforts.

FIG. 4 is a flowchart of one embodiment of S204 in FIG. 2 of the present disclosure;

DETAILED DESCRIPTION OF THE EMBODIMENTS

Figure 1:
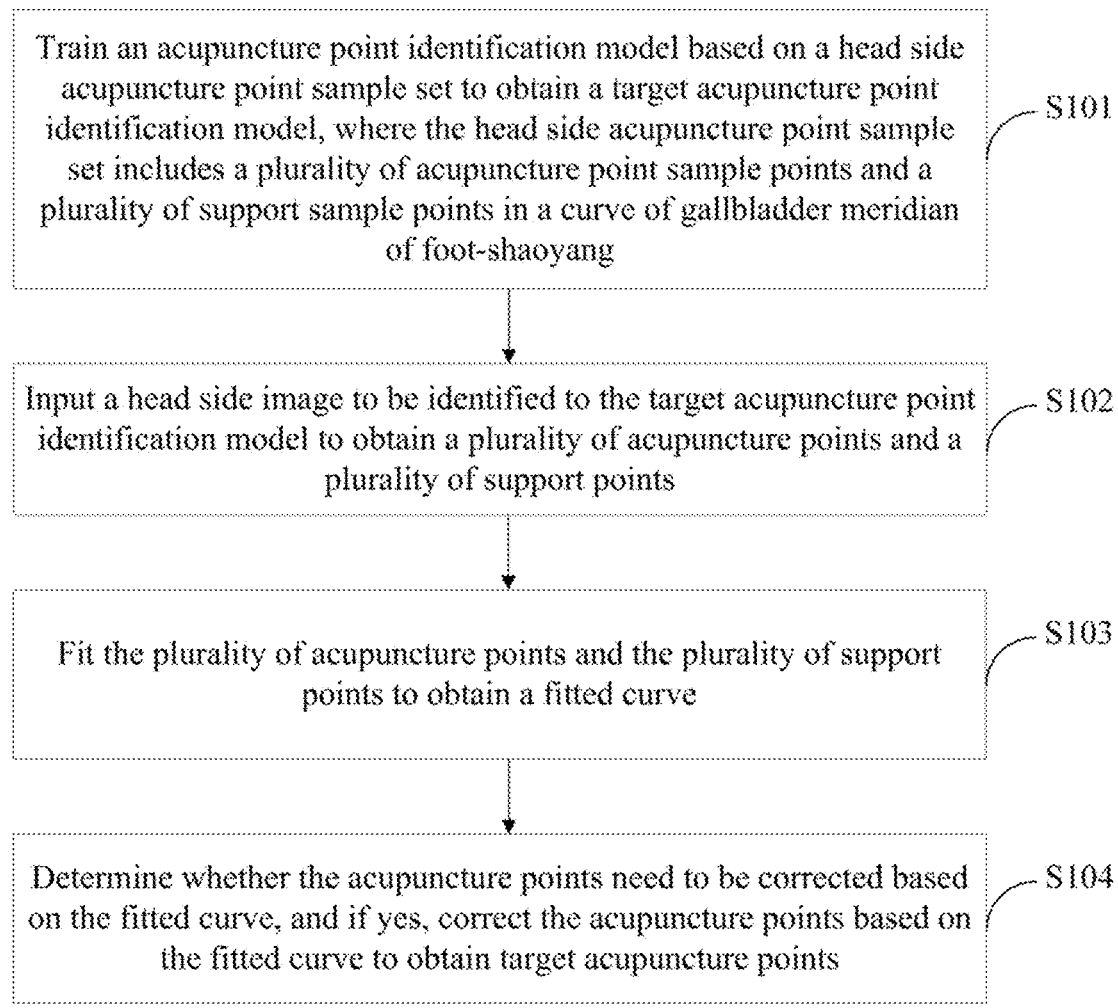
FIG. 1 is a flowchart of one embodiment of a method for locating head side acupuncture points provided by the present disclosure.

The technical solution of the present disclosure will be described below clearly and completely with reference to the drawing in the embodiment of the present disclosure. Apparently, the described embodiments are merely a part rather than all of the embodiments of the present disclosure. All other embodiments obtained by those skilled in the art based on the embodiments of the present disclosure without creative efforts shall fall within the protection scope of the present disclosure.

It should be understood that the schematic accompanying drawings are not drawn based on a scale of a real object. The flowcharts used in the present disclosure show the operations implemented according to some embodiments of the present disclosure. It should be understood that the operations in the flowcharts may be performed out of sequence, and the steps without a logical context relationship may be performed in a reverse sequence or at the same time. Moreover, those skilled in the art may add one or more other operations to the flowcharts or remove one or more operations from the flowcharts based on the content of the present disclosure. Some of the block diagrams shown in the accompanying drawings are functional entities, and do not necessarily correspond to physically or logically independent entities. These functional entities may be implemented in the form of software, or implemented in one or more hardware modules or integrated circuits, or implemented in different networks and/or processor systems and/or microcontroller systems.

When an "embodiment" is mentioned herein, specific features, structures, or characteristics described in conjunction with the embodiment may be included in at least one embodiment of the present disclosure. The term appearing in different parts of the specification does not necessarily refer to the same embodiment or an independent or alternative embodiment exclusive of other embodiments. It may be explicitly or implicitly appreciated by those skilled in the art that the embodiments described herein may be combined with other embodiments.

The present disclosure provides a method and apparatus for locating head side acupuncture points, a moxibustion robot, and a storage medium, which will be separately described below.

FIG. 1 is a flowchart of one embodiment of a method for locating head side acupuncture points provided by the present disclosure. As shown in FIG. 1, the method for locating head side acupuncture points provided by the present disclosure includes the following steps.

In step S101, an acupuncture point identification model is trained based on a head side acupuncture point sample set to obtain a target acupuncture point identification model, where the head side acupuncture point sample set includes a plurality of acupuncture point sample points and a plurality of support sample points in a curve of gallbladder meridian of foot-shaoyang.

In step S102, a head side image to be identified is input to the target acupuncture point identification model to obtain a plurality of acupuncture points and a plurality of support points.

In step S103, the plurality of acupuncture points and of support points are fitted to obtain a fitted curve.

In step S104, whether the acupuncture points require correction based on the fitted curve is determined, and if yes, the acupuncture points are corrected based on the fitted curve to obtain target acupuncture points.

It should be understood that when the acupuncture points do not require correction, the acupuncture points are the target acupuncture points.

The acupuncture point identification model in step S101 may include training, testing, and validation processes. Specifically, the head side acupuncture point sample set is divided into a training set, a test set, and a validation set in a preset ratio, e.g., in a ratio of 8:1:1. The acupuncture point identification model is trained based on the training set. After the training is completed, the performance of the trained acupuncture point identification model is tested. If the acupuncture point identification model passes the test, the acupuncture point identification model is validated based on the validation set. After the acupuncture point identification model passes the validation, the target acupuncture point identification model is obtained, if the acupuncture point identification model fails to pass the test or the validation, the acupuncture point identification model is re-trained based on the training set.

Specifically, the acupuncture point identification model is YOLOv8. YOLOv8 has been improved and innovated on the basis of YOLOv5 and YOLOv7. Anchor-Free is used to replace Anchor-Base and lightweight C2f module is used to replace a C3 module such that the computation load is reduced while the detection accuracy is maintained. Moreover, YOLOv8 uses a spatial pyramid polling-fast (SPPF) module and a path aggregation network-feature pyramid network (PAN-FPN) structure, and improved loss function and matching strategy, such that the detection performance and efficiency are further improved. An execution process of the YOLOv8 network structure is as follows: an input image is converted to a 640*640*3 RGB image and preprocessed (including mosaic enhancement, spatial disturbance, and color disturbance) by a Conv+BatchNorm+SiLU (CBS) module. The CBS module is composed of convolution, normalization, and SiLU activation function, and is configured to extract texture and color information, and solves the problems of gradient vanishing and exploding while improving nonlinear transformation. Next, the C2f module is described, which includes one downsampling convolution kernel and two branches, where one branch is responsible for split and concat operations, and the other branch is responsible for serial-parallel outputs of three Bottleneck networks. Finally, features of the two branches are superposed to obtain an extracted feature result. Input and output channels of a C2f layer have the same size. Finally, a feature image is subjected to a maximum pooling operation by the convolution kernel having the size of 5*5 to extract features. At a Head layer, YOLOv8 uses the decoupling head idea of YOLOX for reference. A regression branch and a prediction branch are separated to extract a class feature and a position feature, respectively.

Compared with the prior art, the method for locating head side acupuncture points provided in the embodiments of the present disclosure uses the target acupuncture point identification model (i.e., a deep learning model) to identify acupuncture points, and can case a doctor's burden and improve the identification efficiency of head side acupuncture points. Moreover, the head side acupuncture point sample set in the embodiments of the present disclosure includes a plurality of acupuncture point sample points and a plurality of support sample points in the curve of gallbladder meridian of foot-shaoyang. That is, the acupuncture point sample points are restrained to be in the curve of gallbladder meridian of foot-shaoyang. The accuracy of the acupuncture points in the head side acupuncture point samples can be guaranteed, and then the accuracy of the acupuncture points identified based on the target acupuncture point identification model can be improved. That is, the locating accuracy of head side acupuncture points is improved.

Further, the embodiments of the present disclosure further involve fitting the identified plurality of acupuncture points and the identified plurality of support points to obtain the fitted curve. The acupuncture points needing to be corrected are corrected based on the fitted curve such that the accuracy of the determined target acupuncture points is further improved. That is, the locating accuracy of head acupuncture points is further improved.

It needs to be noted that, in order to improve the robustness of the target acupuncture point identification model, i.e., to realize accurate identification of a head side image to be identified obtained at any angle by any shooting distance, in some embodiments of the present disclosure, the head side acupuncture point sample set includes a plurality of head side sample images of different persons, a plurality of head side sample images of a same person by a same distance at different angles, and a plurality of head side sample images of a same person by different distances at a same angle.

In the embodiments of the present disclosure, since the head side acupuncture point sample set includes a plurality of head side sample images of different persons and the same person at different angles and at the same angle by different distances, the acupuncture point identification model can learn a plurality of samples so that the obtained target acupuncture point identification model can accurately identify a head side image to be identified at any angle by any distance. The accuracy of the target acupuncture point identification mode is improved.

Further, the head side acupuncture point sample set may further include head side sample images of different hair styles, head styles, skin colors, and light conditions. Thus, the robustness and identification accuracy of the target acupuncture point identification model can be further improved.

Figure 2:
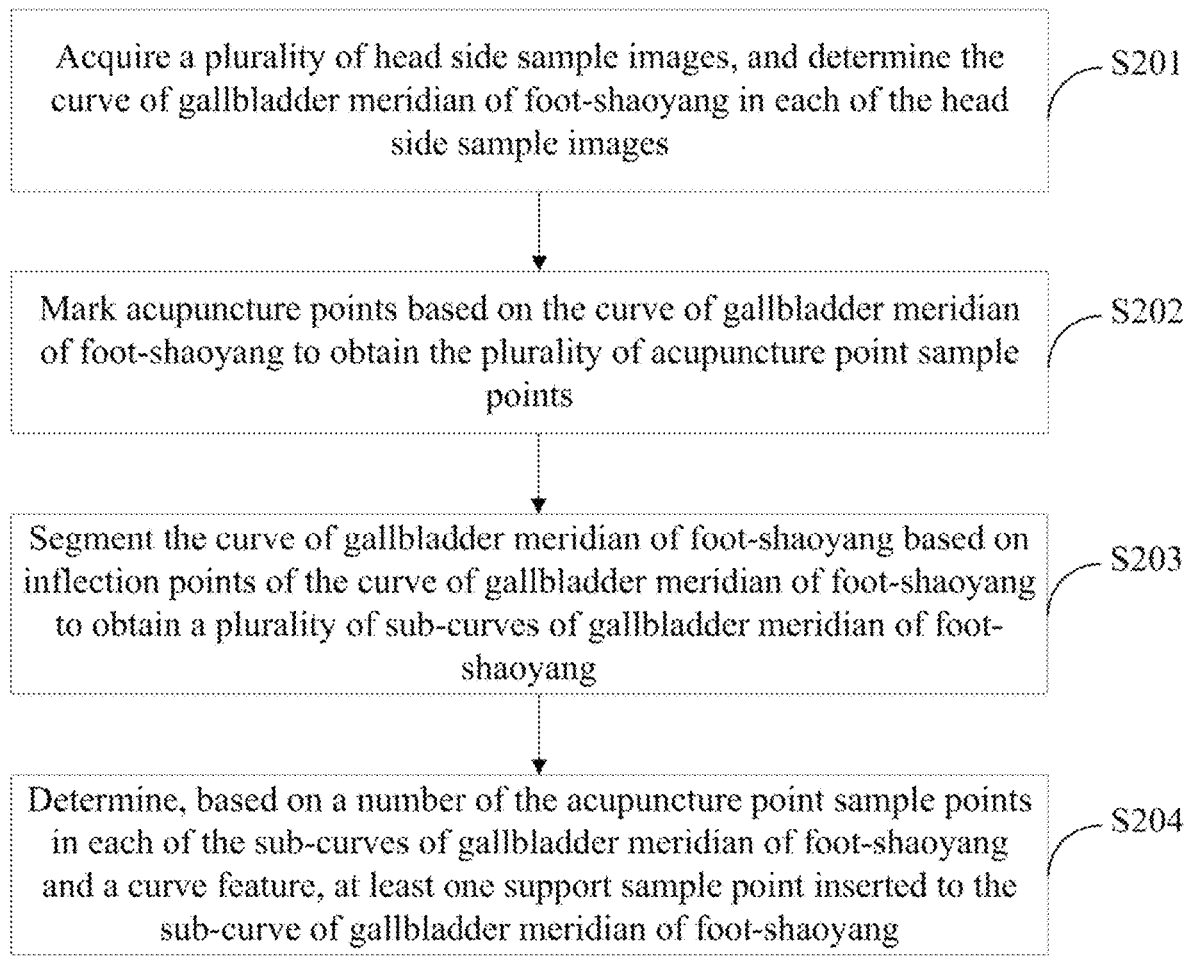
FIG. 2 is a schematic diagram of one embodiment of generating a head side acupuncture point sample set provided by the present disclosure.

Since the fitted curve needs to be obtained based on the acupuncture points and the support points, in order to improve the accuracy of the fitted curve so as to improve the locating accuracy of the head side acupuncture points, it needs to be guaranteed that the acupuncture point sample points and the support sample points in the head side acupuncture point sample set are marked accurately. In order to achieve this purpose, in some embodiments of the present disclosure, as shown in FIG. 2, prior to step S101, the method further includes the following steps.

In step S201, a plurality of head side sample images are acquired, and the curve of gallbladder meridian of foot-shaoyang in each of the head side sample images is determined.

In step S202, acupuncture points are marked based on the curve of gallbladder meridian of foot-shaoyang to obtain the plurality of acupuncture point sample points.

In step S203, the curve of gallbladder meridian of foot-shaoyang is segmented based on inflection points of the curve of gallbladder meridian of foot-shaoyang to obtain a plurality of sub-curves of gallbladder meridian of foot-shaoyang.

In step S204, based on a number of the acupuncture point sample points in each of the sub-curves of gallbladder meridian of foot-shaoyang and a curve feature, at least one support sample point inserted to the sub-curve of gallbladder meridian of foot-shaoyang is determined.

A specific way of marking the acupuncture points in step S202 is as follows: a plurality of acupuncture point sample points are marked in the curve of gallbladder meridian of foot-shaoyang using Labelme marking tool.

Figure 3:
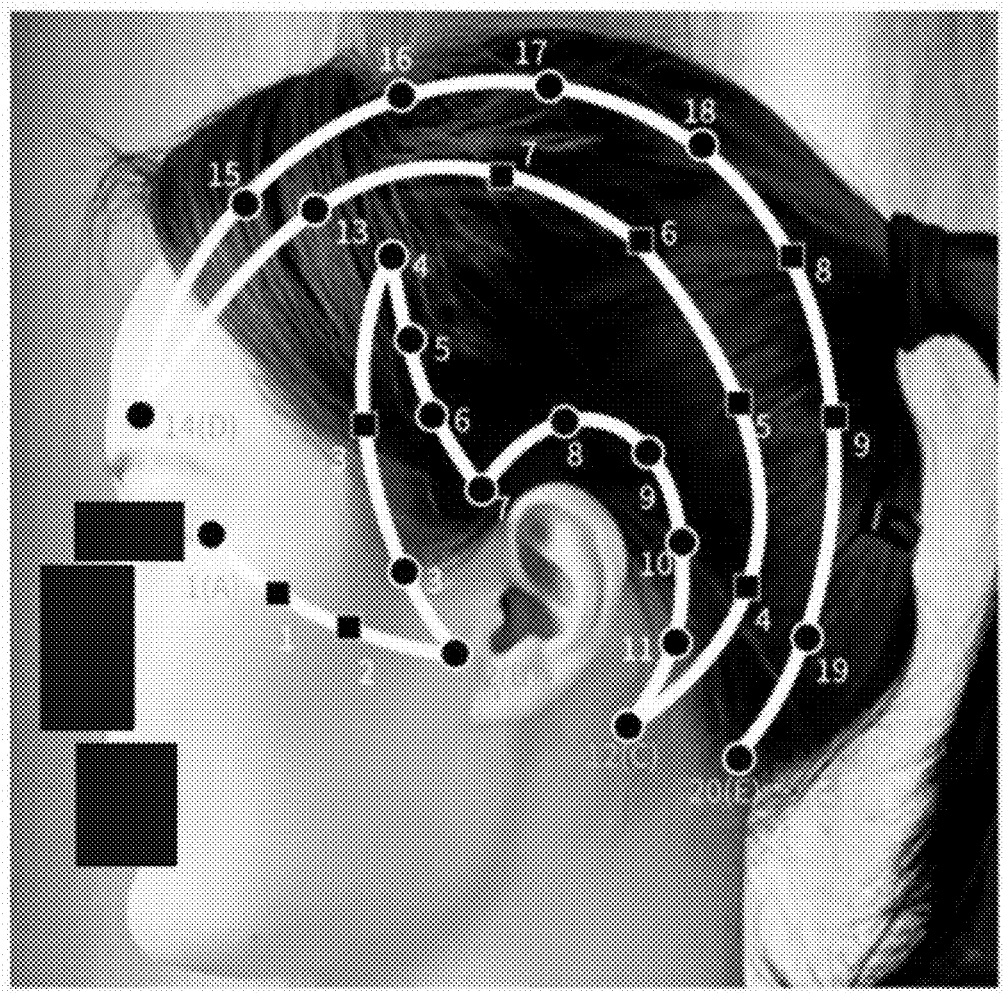
FIG. 3 is a schematic diagram of one embodiment of head side acupuncture point samples provided by the present disclosure.

In a specific embodiment of the present disclosure, as shown in FIG. 3, the curve of gallbladder meridian of foot-shaoyang includes 7 inflection points, which are circular points numbered as 1, 2, 4, 7, 12, 14, and 20. Correspondingly, two adjacent inflection points form a sub-curve of gallbladder meridian of foot-shaoyang, and there are 6 sub-curves of gallbladder meridian of foot-shaoyang in total.

In the embodiments of the present disclosure, the acupuncture points are marked based on the constraint of the curve of gallbladder meridian of foot-shaoyang. The accuracy of the head side acupuncture points identified by the trained target acupuncture point identification model can be improved. Moreover, the embodiments of the present disclosure can ensure the reasonability of the inserted support sample points by determining the number of the inserted support sample points based on the number of acupuncture point sample points and the curve feature, avoiding inserting too many or too few support sample points. The acupuncture point identification efficiency is improved while the acupuncture point identification accuracy is ensured.

In some embodiments of the present disclosure, the curve feature includes a curvature variation rate and a curve length. As shown in FIG. 4, step S204 includes the following steps.

In step S401, when the curvature variation rate of the sub-curve of gallbladder meridian of foot-shaoyang is less than or equal to a first threshold, a total number of support sample points and acupuncture point sample points in the sub-curve of gallbladder meridian of foot-shaoyang is a first threshold number, and a target number of support sample points inserted to the sub-curve of gallbladder meridian of foot-shaoyang is determined based on the first threshold number and the number of the acupuncture point sample points.

In step S402, when the curvature variation rate of the sub-curve of gallbladder meridian of foot-shaoyang is greater than the first threshold and the curve length of the sub-curve of gallbladder meridian of foot-shaoyang is less than or equal to a length threshold, the total number of support sample points and acupuncture point sample points in the sub-curve of gallbladder meridian of foot-shaoyang is a second threshold number, and a target number of support sample points inserted to the sub-curve of gallbladder meridian of foot-shaoyang is determined based on the second threshold number and the number of the acupuncture point sample points.

In step S403, when the curvature variation rate of the sub-curve of gallbladder meridian of foot-shaoyang is greater than the first threshold and the curve length of the sub-curve of gallbladder meridian of foot-shaoyang is greater than the length threshold, the total number of support sample points and acupuncture point sample points in the sub-curve of gallbladder meridian of foot-shaoyang is a third threshold number, and a target number of support sample points inserted to the sub-curve of gallbladder meridian of foot-shaoyang is determined based on the third threshold number and the number of the acupuncture point sample points.

In step S404, the target number of support sample points are inserted to the sub-curve of gallbladder meridian of foot-shaoyang.

The first threshold number is less than the second threshold number, and the second threshold number is less than the third threshold number.

In a specific embodiment of the present disclosure, the first threshold number is 4, the second threshold number is 7, and the third threshold number is 9.

It should be understood that the first threshold, the length threshold, the first threshold number, the second threshold number, and the third threshold number may be adjusted according to an actual application scenario, which will not be redundantly described here one by one.

In a specific embodiment of the present disclosure, as shown in FIG. 3, circular points represent the acupuncture point sample points. The head side sample image includes 20 acupuncture point sample points, numbered as 1 to 20.

The curvature variation rate of the curve between the acupuncture point sample point A and the acupuncture point sample point B is small and less than the first threshold, and the number of support sample points and acupuncture point sample points in the curve segment AB is 4, and 2 support sample points should be inserted between the acupuncture point sample point A and the acupuncture point sample point B.

The curvature variation rate of the curve between the acupuncture point sample point C and the acupuncture point sample point D is large and greater than the first threshold and the curve length between the acupuncture point sample point C and the acupuncture point sample point D is less than the length threshold. The number of support sample points and acupuncture point sample points in the curve segment CD is 7, and 4 support sample points should be inserted between the acupuncture point sample point C and the acupuncture point sample point D.

The curvature variation rate of the curve between the acupuncture point sample point D and the acupuncture point sample point E is large and greater than the first threshold and the curve length between the acupuncture point sample point D and the acupuncture point sample point E is greater than the length threshold. The number of support sample points and acupuncture point sample points in the curve segment DE is 9, and 2 support sample points should be inserted between the acupuncture point sample point D and the acupuncture point sample point E.

It needs to be noted that when a plurality of support sample points need to be inserted, the plurality of support sample points and the plurality of acupuncture point sample points should be distributed as uniformly as possible.

As shown in FIG. 3, the support sample point is represented by a rectangular point. The head side sample image includes 20 acupuncture point sample points in total, numbered as 1 to 20, and 9 support sample points, numbered as 1 to 9.

In some embodiments of the present disclosure, step S103 is as follows: the acupuncture points and the support points are fitted based on the 6 curve segments divided in step S102. That is, 6 fitted curves are obtained by fitting.

However, as can be seen from FIG. 3, the curve formed by these acupuncture points numbered as 7 to 12 has a great change in curvature as a whole, and cannot be expressed by a simple expression. If this segment of curve is fitted as a whole, both of the computation amount and the accuracy of fitting are low. In order to avoid such a problem, in a specific embodiment of the present disclosure, step S103 is as follows:

A plurality of curve segments are determined based on the plurality of acupuncture points and the plurality of support points, where the curve segments are gentle curve segments or circular curve segments; and each of the curve segments includes at least one of the acupuncture points and at least one of the support points.

In the embodiments of the present disclosure, the curve segments are divided into the gentle curve segments and the circular curve segments and then fitted. That is, each curve segment may be expressed using one curve expression. The fitting efficiency is improved while the fitting accuracy is guaranteed.

Specifically, the fitted curve includes 11 curve segments. The acupuncture points and sample points included in the curve segments are as shown in Table 1.

TABLE 1

Curve Segments and Acupuncture Points
and Sample Points Contained Therein

| Curve No. | Acupuncture Point No. | Support Point No. |
|---|---|---|
| 1 | 1, 2 | 1, 2 |
| 2 | 2, 3, 4 | 3 |
| 3 | 4, 5, 6, 7 |  |
| 4 | 7, 8, 9, 10 |  |
| 5 | 10, 11, 12 |  |
| 6 | 12 | 4, 5 |
| 7 |  | 5, 6, 7 |
| 8 | 13, 14 | 7 |
| 9 | 14, 15, 16, 17, 18 |  |
| 10 | 18 | 8, 9 |
| 11 | 19, 20 | 9 |

As can be seen from Table 1, the curve is divided into 11 curve segments for piecewise fitting in the embodiments of the present disclosure.

Since the acupuncture points identified based on the target acupuncture point identification model might not completely coincide with the fitted curve obtained by fitting, the fitted curve represents the gallbladder meridian of foot-shaoyang.

Figure 5:
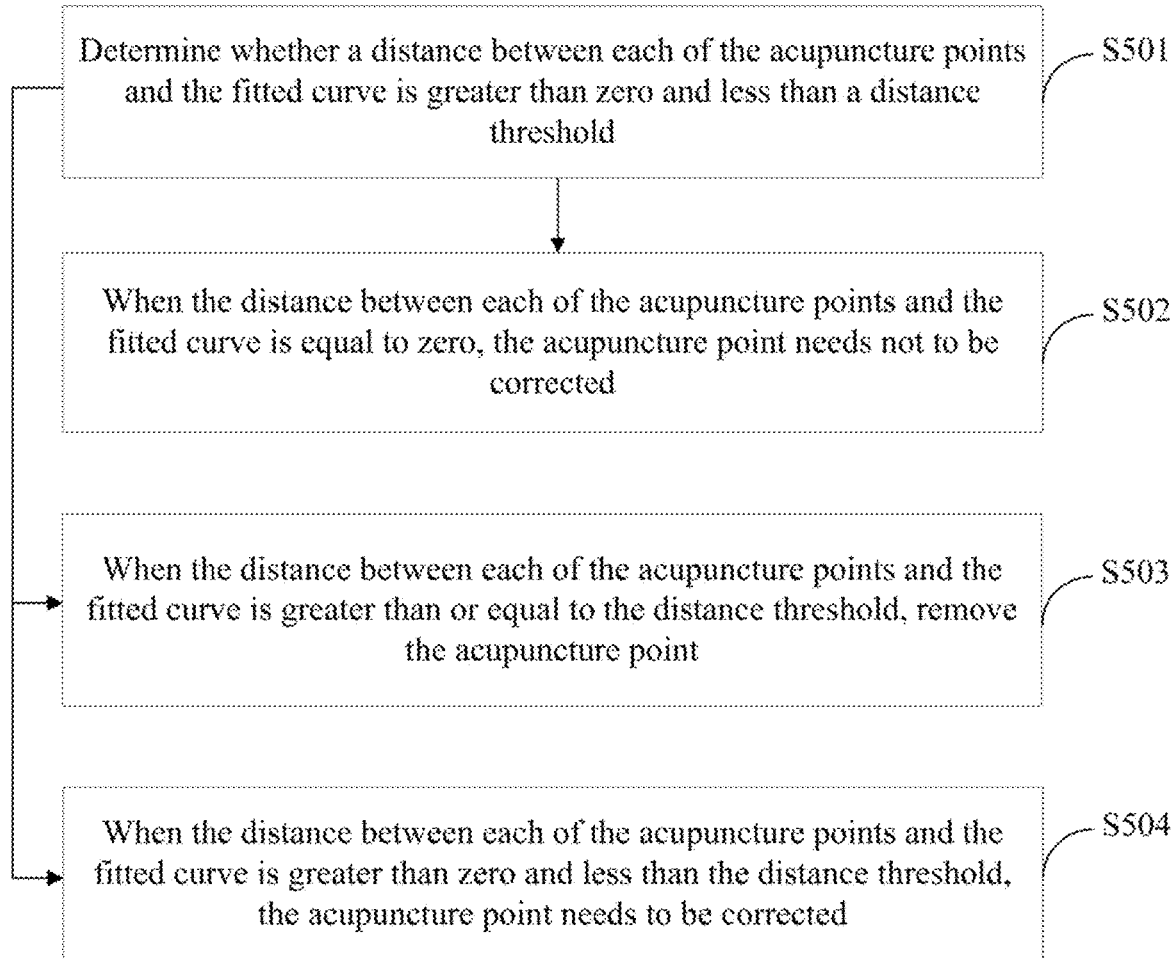
FIG. 5 is a flowchart of one embodiment of determining whether acupuncture points require correction in S104 in FIG. 1 of the present disclosure.

In order to guarantee the locating accuracy of acupuncture points, in a specific embodiment of the present disclosure, as shown in FIG. 5, determining whether the acupuncture points require correction based on the fitted curve in step S104 includes the following steps.

In step S501, whether a distance between each of the acupuncture points and the fitted curve is greater than zero and less than a distance threshold is determined.

In step S502, when the distance between each of the acupuncture points and the fitted curve is equal to zero, the acupuncture point does not require correction.

In step S503, when the distance between each of the acupuncture points and the fitted curve is greater than or equal to the distance threshold, the acupuncture point is removed.

In step S504, when the distance between each of the acupuncture points and the fitted curve is greater than zero and less than the distance threshold, the acupuncture point needs to be corrected.

In the embodiments of the present disclosure, when the distance between each of the acupuncture points and the fitted curve is greater than or equal to the distance threshold, the acupuncture points are removed. Thus, it is avoided that mistakenly identified acupuncture points are mistakenly determined as target acupuncture points. The accuracy of the target acupuncture points is further guaranteed.

Figure 6:
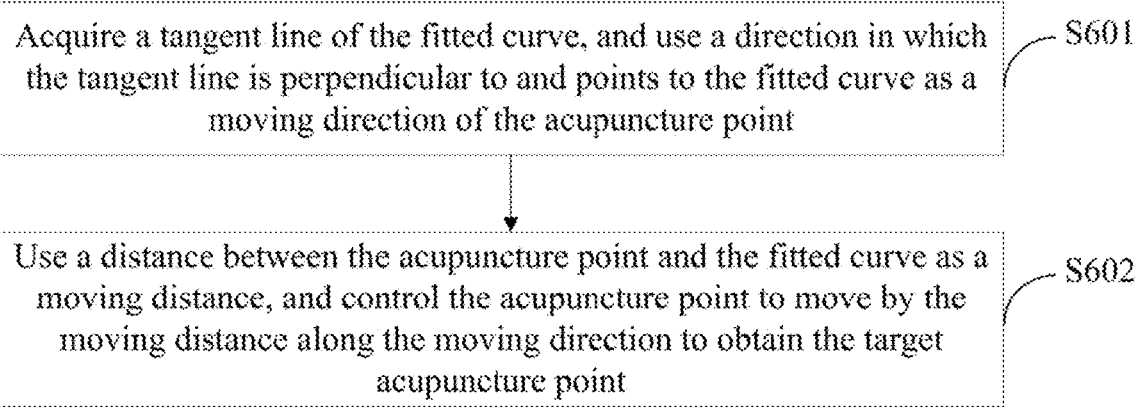
FIG. 6 is a schematic flowchart of one embodiment of correcting acupuncture points in step S104 in FIG. 1 of the present disclosure.

In a specific embodiment of the present disclosure, as shown in FIG. 6, correcting the acupuncture points based on the fitted curve to obtain target acupuncture points in step S104 includes the following steps.

In step S601, a tangent line of the fitted curve is acquired, and a direction in which the tangent line is perpendicular to and points to the fitted curve is used as a moving direction of the acupuncture point.

In step S602, a distance between the acupuncture point and the fitted curve is used as a moving distance, and the acupuncture point is controlled to move by the moving distance along the moving direction to obtain the target acupuncture point.

Figure 7:
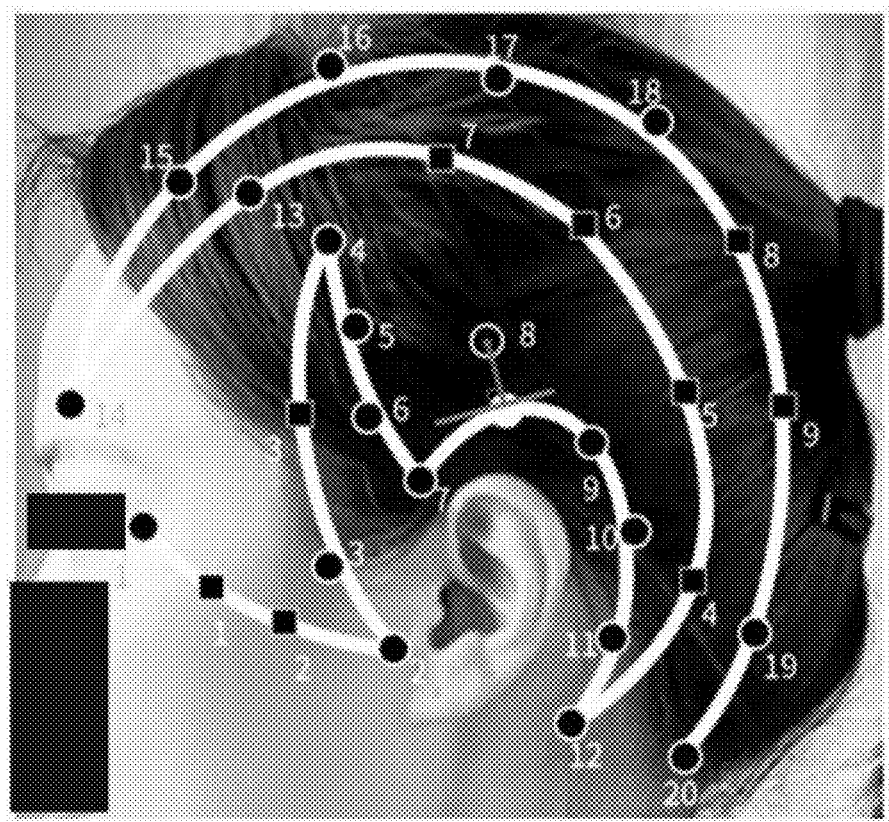
FIG. 7 is a schematic diagram of one embodiment in which there are acupuncture points needing to be corrected provided by the present disclosure.

In a specific embodiment of the present disclosure, as shown in FIG. 7, the identified acupuncture point numbered as 8 does not coincide with the fitted curve segment and does not go beyond a correction range. At this point, the acupuncture point should be moved to the fitted curve segment.

A unit vector u of the moving direction is as follows:

$$u = \langle f'(x_0)/\sqrt{1+f'(x_0)^2}, -1/\sqrt{1+f'(x_0)^2} \rangle$$

The point $(x_0, f(x_0))$ is the closest point on the curve to the point of acupuncture point 8. $f'(x_0)$ is the first-order derivative at this point. The tangent equation at this point is as follows.

$$y - f(x_0) = f'(x_0)(x - x_0)$$

The moving distance d is as follows:

$$d = \left| \frac{f'(x_0)x_8 - y_8 + (f(x_0) - f'(x_0)x_0)}{\sqrt{f'(x_0)^2 + 1}} \right|$$

where $(x_8, y_8)$ is the acupuncture point 8.

In conclusion, the method for locating head side acupuncture points provided in the embodiments of the present disclosure uses deep learning, i.e., the target identification model, to obtain the acupuncture points without human interference, has rapid response capability, and can obtain the acupuncture points in real time dynamically, thus assisting a doctor with diagnosis. In addition, since the acupuncture points are marked and corrected based on the curve of gallbladder meridian of foot-shaoyang, the identification of the head acupuncture points may be constrained by pre-marked meridian curve features, and the locating accuracy of the acupuncture points is improved. Further, the embodiments of the present disclosure do not require the use of an expensive imaging device, and the cost is low. Still further, since the head side acupuncture point sample set includes a plurality of head side sample images of different persons, a plurality of head side sample images of a same person by a same distance at different angles, and a plurality of head side sample images of a same person by different distances at a same angle, the embodiments of the present disclosure can cope with changes of factors such as different head styles, postures, shooting distances, and light conditions and further improve the accuracy of the identified acupuncture points.

Figure 8:
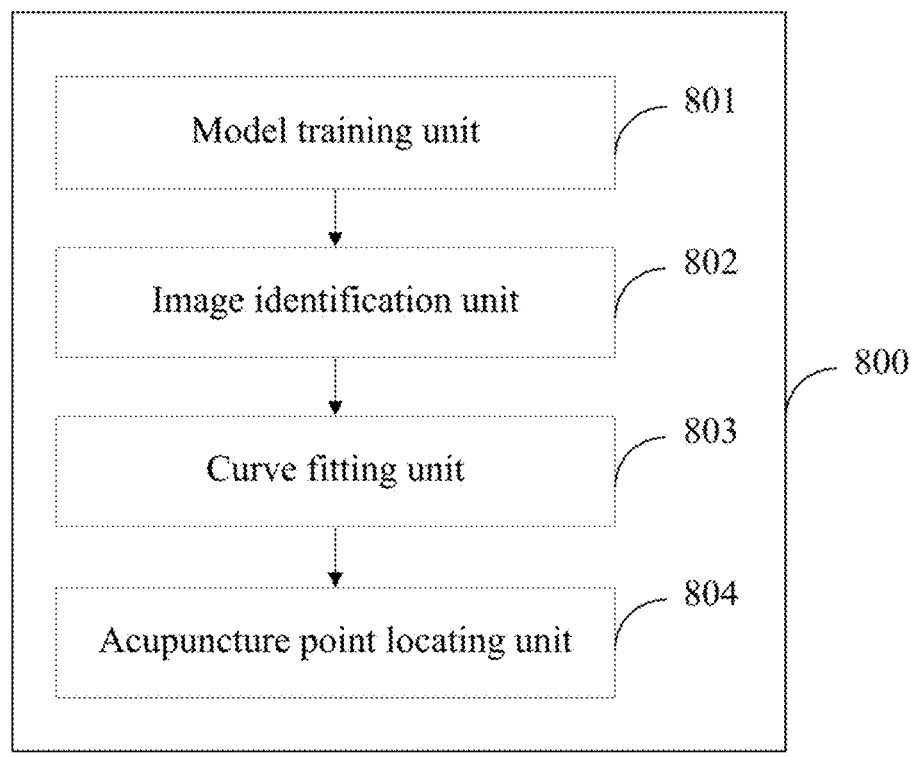
FIG. 8 is a structural schematic diagram of one embodiment of an apparatus for locating head side acupuncture points provided by the present disclosure.

In order to better implement the method for locating head side acupuncture points in the embodiments of the present disclosure, on the basis of the method for locating head side acupuncture points, correspondingly, an embodiment of the present disclosure further provides an apparatus for locating head side acupuncture points. As shown in FIG. 8, the apparatus 800 for locating head side acupuncture points includes:

a model training unit 801 configured to train an acupuncture point identification model based on a head side acupuncture point sample set to obtain a target acupuncture point identification model, the head side acupuncture point sample set includes a plurality of acupuncture point sample points and a plurality of support sample points in a curve of gallbladder meridian of foot-shaoyang;

an image identification unit 802 configured to input a head side image to be identified to the target acupuncture point identification model to obtain a plurality of acupuncture points and a plurality of support points;

a curve fitting unit 803 configured to fit the plurality of acupuncture points and the plurality of support points to obtain a fitted curve; and an acupuncture point locating unit 804 configured to determine whether the acupuncture points require correction based on the fitted curve, and if yes, correct the acupuncture points based on the fitted curve to obtain target acupuncture points.

The apparatus 800 for locating head side acupuncture points provided in the above embodiment can implement the technical solutions described in the above embodiments of the method for locating head side acupuncture points. The specific implementation principles of the above modules or units may be known with reference to the corresponding contents in the above embodiments of the method for locating head side acupuncture points, which will not be redundantly described here.

Figure 9:
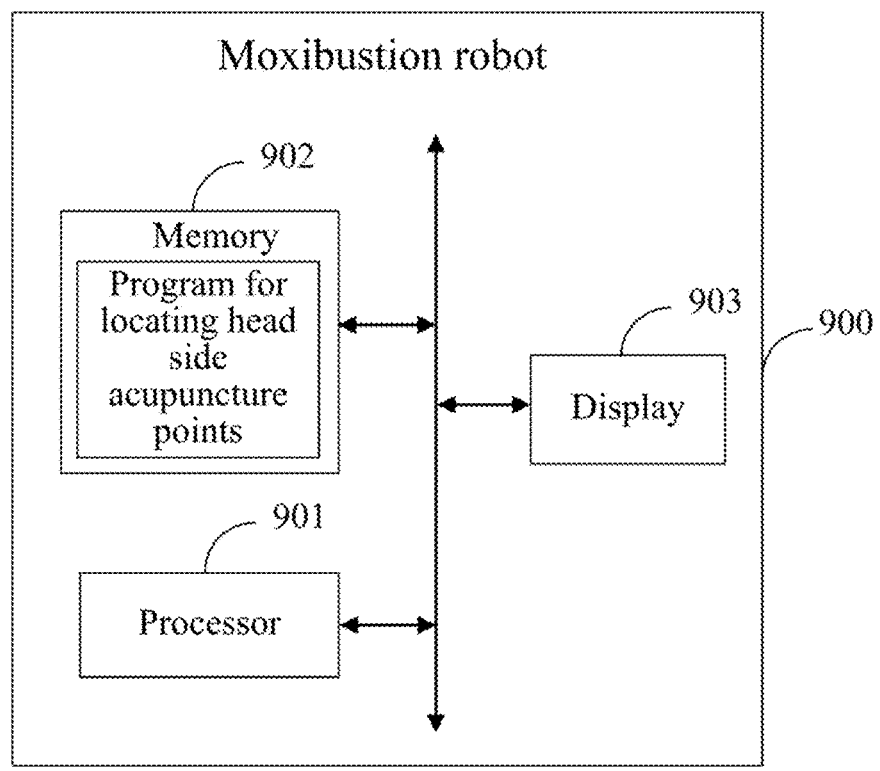
FIG. 9 is a structural schematic diagram of one embodiment of a moxibustion robot provided by the present disclosure.

As shown in FIG. 9, correspondingly, the present disclosure further provides a moxibustion robot 900. The moxibustion robot 900 includes a processor 901, a memory 902, and a display 903. FIG. 9 only shows part of components of the moxibustion robot 900. However, it should be understood that not all the shown components need to be implemented, and more or less components may be implemented instead.

In some embodiments, the processor 901 may be a central processing unit (CPU), a microprocessor, or other data processing chips, and is configured to run a program code stored in the memory 902 or process data, e.g., the method for locating head side acupuncture points in the present disclosure.

In some embodiments of the present disclosure, the processor 901 may be a single server or a server group. The server group may be centralized or distributed. In some embodiments, the processor 901 may be local or remote. In some embodiments, the processor 901 may be implemented in a cloud platform. In an embodiment, the cloud platform may include a private cloud, a public cloud, a hybrid cloud, a community cloud, a distributed cloud, an internal cloud, a multilayer cloud, or the like, or any combination thereof.

In some embodiments, the memory 902 may be an internal storage unit of the moxibustion robot 900, for example, a hard disk or an internal storage of the moxibustion robot 900. In some other embodiments, the memory 902 may also be an external storage device of the moxibustion robot 900, such as a plug-in hard disk, a smart media card (SMC), a secure digital (SD) card, or a flash card that is equipped on the moxibustion robot 900.

Further, the memory 902 may also include both an internal storage unit and an external storage device of the moxibustion robot 900. The memory 902 is configured to store and install application software and various types of data of the moxibustion robot 900.

In some embodiments, the display 903 may be a light-emitting diode (LED) display, a liquid crystal display, a touch liquid crystal display, an organic light-emitting diode (OLED) touch device, etc. The display 903 is configured to display the information of the moxibustion robot 900 and to display a visual user interface. Components 901-903 of the moxibustion robot 900 communicate with one another through a system bus.

In some embodiments of the present disclosure, when the processor 901 executes a program for locating head side acupuncture points in the memory 902, the following steps may be implemented.

An acupuncture point identification model is trained based on a head side acupuncture point sample set to obtain a target acupuncture point identification model, where the head side acupuncture point sample set includes a plurality of acupuncture point sample points and a plurality of support sample points in a curve of gallbladder meridian of foot-shaoyang.

A head side image to be identified is input to the target acupuncture point identification model to obtain a plurality of acupuncture points and a plurality of support points.

The plurality of acupuncture points and of support points are fitted to obtain a fitted curve.

Whether the acupuncture points require correction based on the fitted curve is determined, and if yes, the acupuncture points are corrected based on the fitted curve to obtain target acupuncture points.

It should be understood that when the processor 901 executes the program for locating head side acupuncture points in the memory 902, in addition to the above functions, other functions may also be implemented, as specifically described in the foregoing corresponding method embodiments.

Further, the embodiments of the present disclosure have no specific limitation on the type of the mentioned moxibustion robot 900. The moxibustion robot 900 may be a portable moxibustion robot such as a mobile phone, a tablet personal computer, a personal digital assistant (PDA), a wearable device, and a laptop computer. Exemplary embodiments of the portable moxibustion robot include, but are not limited to, portable moxibustion robots installed with IOS, android, microsoft, or other operating systems. The above-mentioned portable moxibustion robot may also be other portable moxibustion robot. It should be further understood that, in some other embodiments of the present disclosure, the moxibustion robot 900 may also not be a portable moxibustion robot, but be a desktop computer having a touch sensitive surface (e.g., a touch panel).

Correspondingly, an embodiment of the present disclosure further provides a computer readable storage medium configured to store computer readable programs or instructions which, when executed, can implement the steps or functions of the method for locating head side acupuncture points provided in the above method embodiments.

Those skilled in the art can understand that relevant hardware (such as a processor and a controller) can be instructed by computer programs to implement all or part of processes of the method of the above embodiments, and the computer programs can be stored in the computer-readable storage medium. The computer readable storage medium is a magnetic disk, an optical disk, a read-only memory (ROM), a random access memory (RAM), or the like.

The method and apparatus for locating head side acupuncture points, the moxibustion robot, and the storage medium provided in the present disclosure are described above in detail. Several examples are used herein for illustration of the principles and implementations of the present disclosure. The description of the above embodiments is used to help understand the method of the present disclosure and its core ideas. Meanwhile, those skilled in the art can make changes to the specific implementations and the application scope according to the ideas of the present disclosure. In conclusion, the contents of the specification shall not be construed as limitations to the present disclosure.

What is claimed is:

1. A method for locating head side acupuncture points, comprising:
    training an acupuncture point identification model based on a head side acupuncture point sample set to obtain a target acupuncture point identification model, wherein the head side acupuncture point sample set comprises a plurality of acupuncture point sample points and a plurality of support sample points in a curve of gallbladder meridian of foot-shaoyang;
    inputting a head side image to be identified to the target acupuncture point identification model to obtain a plurality of acupuncture points and a plurality of support points;
    fitting the plurality of acupuncture points and the plurality of support points to obtain a fitted curve; and
    determining whether the acupuncture points require correction based on the fitted curve, and if yes, correcting the acupuncture points based on the fitted curve to obtain target acupuncture points;
    before the training an acupuncture point identification model based on a head side acupuncture point sample set, the method further comprises:
    acquiring a plurality of head side sample images, and determining the curve of gallbladder meridian of foot-shaoyang in each of the head side sample images;
    marking acupuncture points based on the curve of gallbladder meridian of foot-shaoyang to obtain the plurality of acupuncture point sample points;
    segmenting the curve of gallbladder meridian of foot-shaoyang based on inflection points of the curve of gallbladder meridian of foot-shaoyang to obtain a plurality of sub-curves of gallbladder meridian of foot-shaoyang; and determining, based on a number of the acupuncture point sample points in each of the sub-curves of gallbladder meridian of foot-shaoyang and a curve feature, at least one support sample point inserted to the sub-curve of gallbladder meridian of foot-shaoyang;

wherein the curve feature comprises a curvature variation rate and a curve length; and the determining, based on a number of the acupuncture point sample points in each of the sub-curves of gallbladder meridian of foot-shaoyang and a curve feature, at least one support sample point inserted to the sub-curve of gallbladder meridian of foot-shaoyang comprises:

when the curvature variation rate of the sub-curve of gallbladder meridian of foot-shaoyang is less than or equal to a first threshold, a total number of support sample points and acupuncture point sample points in the sub-curve of gallbladder meridian of foot-shaoyang being a first threshold number, and determining a target number of support sample points inserted to the sub-curve of gallbladder meridian of foot-shaoyang based on the first threshold number and the number of the acupuncture point sample points;

when the curvature variation rate of the sub-curve of gallbladder meridian of foot-shaoyang is greater than the first threshold and the curve length of the sub-curve of gallbladder meridian of foot-shaoyang is less than or equal to a length threshold, the total number of support sample points and acupuncture point sample points in the sub-curve of gallbladder meridian of foot-shaoyang being a second threshold number, and determining a target number of support sample points inserted to the sub-curve of gallbladder meridian of foot-shaoyang based on the second threshold number and the number of the acupuncture point sample points;

when the curvature variation rate of the sub-curve of gallbladder meridian of foot-shaoyang is greater than the first threshold and the curve length of the sub-curve of gallbladder meridian of foot-shaoyang is greater than the length threshold, the total number of support sample points and acupuncture point sample points in the sub-curve of gallbladder meridian of foot-shaoyang being a third threshold number, and determining a target number of support sample points inserted to the sub-curve of gallbladder meridian of foot-shaoyang based on the third threshold number and the number of the acupuncture point sample points; and inserting the target number of support sample points to the sub-curve of gallbladder meridian of foot-shaoyang;

wherein the first threshold number is less than the second threshold number, and the second threshold number is less than the third threshold number.

2. The method for locating head side acupuncture points according to claim 1, wherein the fitting the plurality of acupuncture points and the plurality of support points to obtain a fitted curve comprises:

determining a plurality of curve segments based on the plurality of acupuncture points and the plurality of support points, wherein the curve segments are gentle curve segments or circular curve segments; and each of the curve segments comprises at least one of the acupuncture points and at least one of the support points.

3. The method for locating head side acupuncture points according to claim 1, wherein the determining whether the acupuncture points require correction based on the fitted curve comprises:

determining whether a distance between each of the acupuncture points and the fitted curve is greater than zero and less than a distance threshold;

when the distance between each of the acupuncture points and the fitted curve is equal to zero, indicating that the acupuncture point does not require correction;

when the distance between each of the acupuncture points and the fitted curve is greater than or equal to the distance threshold, removing the acupuncture point; and when the distance between each of the acupuncture points and the fitted curve is greater than zero and less than the distance threshold, indicating that the acupuncture point requires correction.

4. The method for locating head side acupuncture points according to claim 1, wherein the correcting the acupuncture points based on the fitted curve to obtain target acupuncture points comprises:

acquiring a tangent line of the fitted curve, and using a direction in which the tangent line is perpendicular to and points to the fitted curve as a moving direction of the acupuncture point; and using a distance between the acupuncture point and the fitted curve as a moving distance, and controlling the acupuncture point to move by the moving distance along the moving direction to obtain the target acupuncture point.

5. The method for locating head side acupuncture points according to claim 1, wherein the head side acupuncture point sample set comprises a plurality of head side sample images of different persons, a plurality of head side sample images of a same person by a same distance at different angles, and a plurality of head side sample images of a same person by different distances at a same angle.

6. An apparatus for locating head side acupuncture points, comprising:

a model training unit configured to train an acupuncture point identification model based on a head side acupuncture point sample set to obtain a target acupuncture point identification model, wherein the head side acupuncture point sample set comprises a plurality of acupuncture point sample points and a plurality of support sample points in a curve of gallbladder meridian of foot-shaoyang;

an image identification unit configured to input a head side image to be identified to the target acupuncture point identification model to obtain a plurality of acupuncture points and a plurality of support points;

a curve fitting unit configured to fit the plurality of acupuncture points and the plurality of support points to obtain a fitted curve; and an acupuncture point locating unit configured to determine whether the acupuncture points require correction based on the fitted curve, and if yes, correct the acupuncture points based on the fitted curve to obtain target acupuncture points;

before the training an acupuncture point identification model based on a head side acupuncture point sample set, further comprising:

acquiring a plurality of head side sample images, and determining the curve of gallbladder meridian of foot-shaoyang in each of the head side sample images;

marking acupuncture points based on the curve of gallbladder meridian of foot-shaoyang to obtain the plurality of acupuncture point sample points;

segmenting the curve of gallbladder meridian of foot-shaoyang based on inflection points of the curve of gallbladder meridian of foot-shaoyang to obtain a plurality of sub-curves of gallbladder meridian of foot-shaoyang; and determining, based on a number of the acupuncture point sample points in each of the sub-curves of gallbladder meridian of foot-shaoyang and a curve feature, at least one support sample point inserted to the sub-curve of gallbladder meridian of foot-shaoyang;

wherein the curve feature comprises a curvature variation rate and a curve length; and the determining, based on a number of the acupuncture point sample points in each of the sub-curves of gallbladder meridian of foot-shaoyang and a curve feature, at least one support sample point inserted to the sub-curve of gallbladder meridian of foot-shaoyang comprises:

when the curvature variation rate of the sub-curve of gallbladder meridian of foot-shaoyang is less than or equal to a first threshold, a total number of support sample points and acupuncture point sample points in the sub-curve of gallbladder meridian of foot-shaoyang being a first threshold number, and determining a target number of support sample points inserted to the sub-curve of gallbladder meridian of foot-shaoyang based on the first threshold number and the number of the acupuncture point sample points;

when the curvature variation rate of the sub-curve of gallbladder meridian of foot-shaoyang is greater than the first threshold and the curve length of the sub-curve of gallbladder meridian of foot-shaoyang is less than or equal to a length threshold, the total number of support sample points and acupuncture point sample points in the sub-curve of gallbladder meridian of foot-shaoyang being a second threshold number, and determining a target number of support sample points inserted to the sub-curve of gallbladder meridian of foot-shaoyang based on the second threshold number and the number of the acupuncture point sample points;

when the curvature variation rate of the sub-curve of gallbladder meridian of foot-shaoyang is greater than the first threshold and the curve length of the sub-curve of gallbladder meridian of foot-shaoyang is greater than the length threshold, the total number of support sample points and acupuncture point sample points in the sub-curve of gallbladder meridian of foot-shaoyang being a third threshold number, and determining a target number of support sample points inserted to the sub-curve of gallbladder meridian of foot-shaoyang based on the third threshold number and the number of the acupuncture point sample points; and inserting the target number of support sample points to the sub-curve of gallbladder meridian of foot-shaoyang;

wherein the first threshold number is less than the second threshold number, and the second threshold number is less than the third threshold number.

7. A moxibustion robot, comprising a memory and a processor, wherein:
the memory is configured to store a program; and
the processor is coupled with the memory and configured to execute the program stored in the memory to implement the steps of the method for locating head side acupuncture points according to claim 1.

8. A non-transitory computer readable storage medium, storing a program or instructions which, when executed by a processor, cause(s) the steps of the method for locating head side acupuncture points according to claim 1 to be implemented.

9. A moxibustion robot, comprising a memory and a processor, wherein:
the memory is configured to store a program; and
the processor is coupled with the memory and configured to execute the program stored in the memory to implement the steps of the method for locating head side acupuncture points according to claim 2.

10. A moxibustion robot, comprising a memory and a processor, wherein:
the memory is configured to store a program; and
the processor is coupled with the memory and configured to execute the program stored in the memory to implement the steps of the method for locating head side acupuncture points according to claim 3.

11. A moxibustion robot, comprising a memory and a processor, wherein:
the memory is configured to store a program; and
the processor is coupled with the memory and configured to execute the program stored in the memory to implement the steps of the method for locating head side acupuncture points according to claim 4.

12. A moxibustion robot, comprising a memory and a processor, wherein:
the memory is configured to store a program; and
the processor is coupled with the memory and configured to execute the program stored in the memory to implement the steps of the method for locating head side acupuncture points according to claim 5.

13. A non-transitory computer readable storage medium, storing a program or instructions which, when executed by a processor, cause(s) the steps of the method for locating head side acupuncture points according to claim 2 to be implemented.

14. A non-transitory computer readable storage medium, storing a program or instructions which, when executed by a processor, cause(s) the steps of the method for locating head side acupuncture points according to claim 3 to be implemented.

15. A non-transitory computer readable storage medium, storing a program or instructions which, when executed by a processor, cause(s) the steps of the method for locating head side acupuncture points according to claim 4 to be implemented.

16. A non-transitory computer readable storage medium, storing a program or instructions which, when executed by a processor, cause(s) the steps of the method for locating head side acupuncture points according to claim 5 to be implemented.

* * * * *